United States Patent
Gao et al.

(10) Patent No.: US 9,133,095 B2
(45) Date of Patent: Sep. 15, 2015

(54) CHRYSENE COMPOUNDS FOR LUMINESCENT APPLICATIONS

(75) Inventors: Weiying Gao, Landenberg, PA (US); Norman Herron, Newark, DE (US); Jeffrey A. Merlo, Wilmington, DE (US); Vsevolod Rostovtsev, Swarthmore, PA (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 937 days.

(21) Appl. No.: 13/379,807

(22) PCT Filed: Jun. 30, 2010

(86) PCT No.: PCT/US2010/040578
§ 371 (c)(1),
(2), (4) Date: Dec. 21, 2011

(87) PCT Pub. No.: WO2011/002870
PCT Pub. Date: Jan. 6, 2011

(65) Prior Publication Data
US 2012/0146008 A1   Jun. 14, 2012

Related U.S. Application Data

(60) Provisional application No. 61/222,244, filed on Jul. 1, 2009.

(51) Int. Cl.
*H01L 51/54* (2006.01)
*C07D 403/12* (2006.01)
*H01L 51/46* (2006.01)
*C07C 211/61* (2006.01)
*C09K 11/06* (2006.01)
*H01L 51/00* (2006.01)
*H01L 51/50* (2006.01)
(Continued)

(52) U.S. Cl.
CPC .............. *C07C 211/61* (2013.01); *C09B 57/00* (2013.01); *C09B 57/008* (2013.01); *C09K 11/06* (2013.01); *H01L 51/006* (2013.01); *H01L 51/5012* (2013.01); *H05B 33/14* (2013.01); *C07C 2103/48* (2013.01); *C09K 2211/1007* (2013.01); *C09K 2211/1011* (2013.01); *C09K 2211/1014* (2013.01); *C09K 2211/1029* (2013.01)

(58) Field of Classification Search
None
See application file for complete search history.

(56) References Cited

U.S. PATENT DOCUMENTS 4,043,311 A   8/1977   Bieri
5,247,190 A   9/1993   Friend et al.
(Continued)

FOREIGN PATENT DOCUMENTS

EP   443861 B1   7/1995
EP   1061112 A1   12/2000
(Continued)

OTHER PUBLICATIONS

Beckmann et al., "Methyl Reorientation in Solid 3-ethychrysene and 3-isopropylesene," Solid State Nuclear Magnetic Resonance, 1998; vol. 12; pp. 251-256.
(Continued)

*Primary Examiner* — J. L. Yang

(57) ABSTRACT

This disclosure relates to chrysene compounds that are useful in electroluminescent applications. It also relates to electronic devices in which the active layer includes such a chrysene compound.

5 Claims, 1 Drawing Sheet

(51) Int. Cl.
*H05B 33/14* (2006.01)
*C09B 57/00* (2006.01)

(56) References Cited

U.S. PATENT DOCUMENTS

| | | | |
|---|---|---|---|
| 5,408,109 | A | 4/1995 | Heeger et al. |
| 6,670,645 | B2 | 12/2003 | Grushin et al. |
| 6,852,429 | B1 | 2/2005 | Li et al. |
| 6,875,524 | B2 | 4/2005 | Hatwar et al. |
| 7,075,102 | B2 | 7/2006 | Grushin et al. |
| 7,173,131 | B2 | 2/2007 | Saitoh et al. |
| 7,358,409 | B2 | 4/2008 | Saitoh et al. |
| 7,375,250 | B2 | 5/2008 | Saitoh et al. |
| 7,491,450 | B2 | 2/2009 | Okinaka et al. |
| 7,651,788 | B2 | 1/2010 | Seo et al. |
| 7,709,104 | B2 | 5/2010 | Saitoh et al. |
| 2002/0076576 | A1 | 6/2002 | Li |
| 2003/0072966 | A1 | 4/2003 | Hosokawa et al. |
| 2003/0138657 | A1 | 7/2003 | Li |
| 2004/0102577 | A1 | 5/2004 | Hsu et al. |
| 2004/0106003 | A1 | 6/2004 | Chen et al. |
| 2004/0121184 | A1 | 6/2004 | Thompson et al. |
| 2004/0127637 | A1 | 7/2004 | Hsu et al. |
| 2005/0031898 | A1 | 2/2005 | Li et al. |
| 2005/0064233 | A1 | 3/2005 | Matsuura et al. |
| 2005/0158577 | A1 | 7/2005 | Ishibashi et al. |
| 2005/0184287 | A1 | 8/2005 | Herron et al. |
| 2005/0205860 | A1 | 9/2005 | Hsu et al. |
| 2006/0033421 | A1 | 2/2006 | Matsuura et al. |
| 2006/0052641 | A1 | 3/2006 | Funahashi |
| 2006/0103298 | A1 | 5/2006 | Lee |
| 2006/0113528 | A1 | 6/2006 | Okinaka et al. |
| 2006/0115678 | A1 | 6/2006 | Saitoh et al. |
| 2006/0121312 | A1 | 6/2006 | Yamada et al. |
| 2006/0152146 | A1 | 7/2006 | Funahashi |
| 2006/0159838 | A1 | 7/2006 | Kowalski et al. |
| 2006/0194074 | A1 | 8/2006 | Funahashi |
| 2006/0210830 | A1 | 9/2006 | Funahashi |
| 2006/0267488 | A1 | 11/2006 | Saitoh et al. |
| 2007/0063638 | A1 | 3/2007 | Tokairin et al. |
| 2007/0114917 | A1 | 5/2007 | Funahashi |
| 2007/0155991 | A1 | 7/2007 | Funahashi |
| 2007/0236137 | A1 | 10/2007 | Funahashi |
| 2007/0255076 | A1 | 11/2007 | Ito et al. |
| 2007/0292713 | A9 | 12/2007 | Dobbs et al. |
| 2007/0298530 | A1 | 12/2007 | Feehery |
| 2008/0049413 | A1 | 2/2008 | Jinde et al. |
| 2008/0071049 | A1 | 3/2008 | Radu et al. |
| 2008/0191614 | A1 | 8/2008 | Kim et al. |
| 2008/0233433 | A1 | 9/2008 | Igarashi et al. |
| 2008/0286605 | A1 | 11/2008 | Takeda |
| 2008/0303425 | A1 | 12/2008 | Rostovtsev et al. |
| 2008/0303428 | A1 | 12/2008 | Rostovtsev et al. |
| 2008/0315754 | A1 | 12/2008 | Kawamura et al. |
| 2009/0058279 | A1 | 3/2009 | Takeda |
| 2009/0134781 | A1 | 5/2009 | Jang et al. |
| 2011/0147718 | A1 | 6/2011 | Howard, Jr. et al. |

FOREIGN PATENT DOCUMENTS

| | | |
|---|---|---|
| EP | 1561794 A1 | 8/2005 |
| EP | 2067766 A1 | 6/2009 |
| EP | 2067767 A1 | 6/2009 |
| JP | 07249490 A | 9/1995 |
| JP | 2004010550 A | 1/2004 |
| JP | 2006052323 A | 2/2006 |
| JP | 2006151844 A | 6/2006 |
| JP | 2006219392 A | 8/2006 |
| JP | 2007186449 A | 7/2007 |
| JP | 2009161470 A | 7/2009 |
| KR | 1020090046731 A | 5/2009 |
| KR | 1020090086015 A | 8/2009 |
| KR | 1020090086920 A | 8/2009 |
| KR | 1020090093897 A | 9/2009 |
| WO | 03040257 A1 | 5/2003 |
| WO | 03063555 A1 | 7/2003 |
| WO | 2004016710 A1 | 2/2004 |
| WO | 2005052027 A1 | 6/2005 |
| WO | 2006025273 A1 | 3/2006 |
| WO | 2007021117 A1 | 2/2007 |
| WO | 2007100096 A1 | 9/2007 |
| WO | 2007105917 A1 | 9/2007 |
| WO | 2007108666 A1 | 9/2007 |
| WO | 2008149968 A1 | 12/2008 |
| WO | 2009018009 A1 | 2/2009 |
| WO | 2009028902 A2 | 3/2009 |
| WO | 2009055628 A1 | 4/2009 |

OTHER PUBLICATIONS

Gustafsson et al., "Flexible Light-Emitting Diodes Made From Soluble Conducting Polymers," Nature, 1992, vol. 357, pp. 477-479.
Kodomari et al., "Selective Halogenation o f Aromatic Hydrocarbons," Journal of Organic Chemistry,1988, vol. 53, p. 2093.
Markus et al—Electronics and Nuleonics Dictionary, pp. 470-471 & 476 (McGraw-Hill 1966).
Mueller et al., "Synthesis and Characterization of Soluble Oligo(9,10-anthrylene)s," Chemische Berichte, 1994, 127, pp. 437-444.
Negishi et al; III.2.15 Palladium Catalyzed Conjugate Substitution; Handbook of Organopalladium Chemsitry for Organic Synthesis, 2000, vol. 1, pp. 767-789.
Wang—Photoconductive Material, Kirk-Othmer Encyclopedia of Chemical Technology Fourth Edition, 1996, vol. 18, pp. 837-860.
International Search Report Korean Intellectual Property Office, Daejeon, Republic of Korea, Hyun Shik Oh, Authorized Offier, Dec. 24, 2010, in PCT/US/035364, PCT counterpart of co-pending U.S. Appl. No. 13/265,025.
International Search Report, European Patent Office, Rijswijk NL, in PCT/2008/063811, PCT copending U.S. Appl. No. 12/121,883, Csaba A. Nemes, Authorized Officer, Jul. 29, 2008.
International Search Report, European Patent Office, Rijswijk NL, in PCT/2008/065091, PCT copending U.S. Appl. No. 12/129,760, Alina Sen, Authorized Officer, Oct. 23, 2008.
International Search Report, European Patent Office, Rijswijk NL, in PCT/2008/065187, PCT copending U.S. Appl. No. 12/129,753, Cecile Vanier, Authorized Officer, Feb. 10, 2008.
International Search Report, Korean Intellectual Property Office, Daejeon, Republic of Korea, in PCT/2009/065163, PCT copending U.S. Appl. No. 13/120,001, Hyun Shik Oh, Authorized Officer, May 19, 2010.
International Search Report, Korean Intellectual Property Office, Daejeon, Republic of Korea, in PCT/2009/068928, PCT copending U.S. Appl. No. 12/643,511, Hyun Shik Oh, Authorized Officer, Aug. 17, 2010.
International Search Report, Korean Intellectual Property Office, Daejeon, Republic of Korea, in PCT/2009/068956, PCT copending U.S. Appl. No. 12/643,487, Hyun Shik Oh, Authorized Officer, Sep. 6, 2010.
International Search Report, Korean Intellectual Property Office, Daejeon, Republic of Korea, in PCT/2010/040578, PCT copending application, Hyun Shik Oh, Authorized Officer, Feb. 11, 2011.

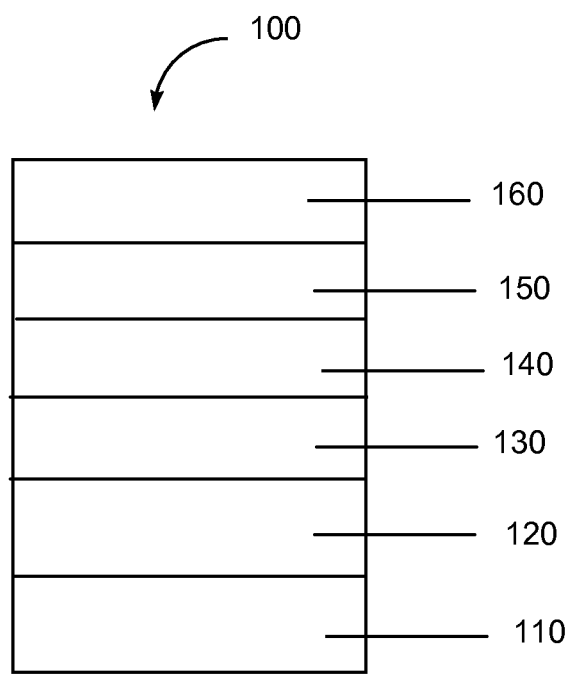

CHRYSENE COMPOUNDS FOR LUMINESCENT APPLICATIONS

RELATED APPLICATION

This application claims priority under 35 U.S.C. §119(e) from Provisional Application No. 61/222,244 filed Jul. 1, 2009 which is incorporated by reference in its entirety.

BACKGROUND

1. Field of the Disclosure

This disclosure relates to electroluminescent chrysene compounds. It also relates to electronic devices in which the active layer includes such a chrysene compound.

2. Description of the Related Art

Organic electronic devices that emit light, such as light-emitting diodes that make up displays, are present in many different kinds of electronic equipment. In all such devices, an organic active layer is sandwiched between two electrical contact layers. At least one of the electrical contact layers is light-transmitting so that light can pass through the electrical contact layer. The organic active layer emits light through the light-transmitting electrical contact layer upon application of electricity across the electrical contact layers.

It is well known to use organic electroluminescent compounds as the active component in light-emitting diodes. Simple organic molecules such as anthracene, thiadiazole derivatives, and coumarin derivatives are known to show electroluminescence. Semiconductive conjugated polymers have also been used as electroluminescent components, as has been disclosed in, for example, U.S. Pat. No. 5,247,190, U.S. Pat. No. 5,408,109, and Published European Patent Application 443 861.

However, there is a continuing need for electroluminescent compounds, especially compounds that are blue-emitting.

SUMMARY

There is provided a compound having Formula I:

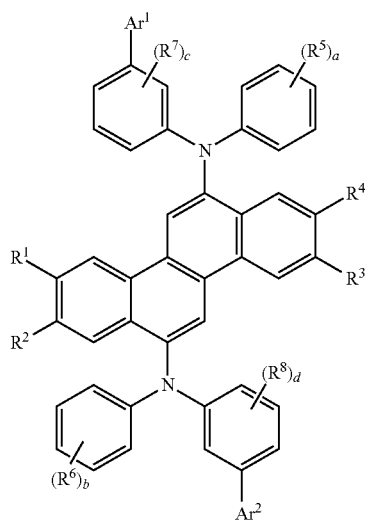

Formula I wherein:
$R^1$, $R^2$, $R^3$ and W are the same or different and are selected from the group consisting of H, D, alkyl, and silyl, where $R^1$ and $R^2$ groups or $R^3$ and $R^4$ groups may be joined together to form a 5- or 6-membered aliphatic ring;

$R^5$ and $R^6$ are the same or different and are selected from the group consisting of D, alkyl, silyl, phenyl, naphthyl, N-carbazolyl, and fluorenyl;

$R^7$ and $R^8$ are the same or different at each occurrence and are selected from the group consisting of D, alkyl, alkoxy, silyl, siloxane, phenyl, biphenyl, and N-carbazolyl, or two adjacent $R^7$ groups or two adjacent $R^8$ groups can join together to form a naphthyl group;

$Ar^1$ and $Ar^2$ are the same or different and are aryl groups;

a and b are the same or different and are an integer from 1-5; and c and d are the same or different at each occurrence and are an integer from 0-4.

There is also provided the compound of Formula I, wherein $R^7$ and $R^8$ are selected from the group consisting of D, phenyl, biphenyl, and N-carbazolyl, or two adjacent $R^7$ groups or two adjacent $R^8$ groups can join together to form a naphthyl group.

There is also provided an electronic device comprising an active layer comprising the compound of Formula I.

BRIEF DESCRIPTION OF THE DRAWINGS

Embodiments are illustrated in the accompanying figures to improve understanding of concepts as presented herein.

FIG. 1 includes an illustration of one example of an organic electronic device.

Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

Many aspects and embodiments are disclosed herein and are exemplary and not limiting. After reading this specification, skilled artisans appreciate that other aspects and embodiments are possible without departing from the scope of the invention.

Other features and benefits of any one or more of the embodiments will be apparent from the following detailed description, and from the claims. The detailed description first addresses Definitions and Clarification of Terms followed by the Chrysene Compound, the Electronic Device, and finally Examples.

1. Definitions and Clarification of Terms

Before addressing details of embodiments described below, some terms are defined or clarified.

As used herein, the term "aliphatic ring" is intended to mean a cyclic group that does not have delocalized pi electrons. In some embodiments, the aliphatic ring has no unsaturation. In some embodiments, the ring has one double or triple bond.

The term "alkyl" is intended to mean a group derived from an aliphatic hydrocarbon having one point of attachment, and includes a linear, a branched, or a cyclic group. The term is intended to include heteroalkyls. The term "hydrocarbon alkyl" refers to an alkyl group having no heteroatoms. In some embodiments, an alkyl group has from 1-20 carbon atoms.

The term "aryl" is intended to mean a group derived from an aromatic hydrocarbon having one point of attachment. The term includes groups which have a single ring and those which have multiple rings which can be joined by a single bond or fused together. The term is intended to include heteroaryls. The term "arylene" is intended to mean a group derived from an aromatic hydrocarbon having two points of attachment. In some embodiments, an aryl group has from 3-60 carbon atoms.

The term "branched alkyl" refers to an alkyl group having at least one secondary or tertiary carbon. The term "secondary alkyl" refers to a branched alkyl group having a secondary carbon atom. The term "tertiary alkyl" refers to a branched alkyl group having a tertiary carbon atom. In some embodiments, the branched alkyl group is attached via a secondary or tertiary carbon.

The term "compound" is intended to mean an electrically uncharged substance made up of molecules that further consist of atoms, wherein the atoms cannot be separated by physical means. The phrase "adjacent to," when used to refer to layers in a device, does not necessarily mean that one layer is immediately next to another layer. On the other hand, the phrase "adjacent R groups," is used to refer to R groups that are next to each other in a chemical formula (i.e., R groups that are on atoms joined by a bond). The prefix "fluoro" indicates that one or more carbon atoms have been replaced with fluorine.

The prefix "hetero" indicates that one or more carbon atoms have been replaced with a different atom. In some embodiments, the different atom is N, O, or S.

The term "layer" is used interchangeably with the term "film" and refers to a coating covering a desired area. The term is not limited by size. The area can be as large as an entire device or as small as a specific functional area such as the actual visual display, or as small as a single sub-pixel. Layers and films can be formed by any conventional deposition technique, including vapor deposition, liquid deposition (continuous and discontinuous techniques), and thermal transfer. Continuous deposition techniques, include but are not limited to, spin coating, gravure coating, curtain coating, dip coating, slot-die coating, spray coating, and continuous nozzle coating. Discontinuous deposition techniques include, but are not limited to, ink jet printing, gravure printing, and screen printing.

The term "organic electronic device" or sometimes just "electronic device" is intended to mean a device including one or more organic semiconductor layers or materials.

The term "photoactive" refers to any material that exhibits electroluminescence and/or photosensitivity.

The term "siloxane" refers to the group (RO)$_3$Si—, where R is H, D C1-20 alkyl, or fluoroalkyl.

The term "silyl" refers to the group R$_3$Si—, where R is H, D, C1-20 alkyl, fluoroalkyl, or aryl. In some embodiments, one or more carbons in an R alkyl group are replaced with Si. In some embodiments, the silyl groups are (hexyl)$_2$Si(CH$_3$) CH$_7$CH$_2$Si(CH$_3$)$_2$— and [CF$_3$(CF$_2$)$_6$CH$_2$CH$_2$]$_2$Si(CH$_3$)—.

All groups can be substituted or unsubstituted unless otherwise indicated. In some embodiments, the substituents are selected from the group consisting of D, halide, alkyl, alkoxy, silyl, siloxane, aryl, and cyano. All groups may be partially or fully deuterated.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control.

In addition, the materials, methods, and examples are illustrative only and not intended to be limiting.

The IUPAC numbering system is used throughout, where the groups from the Periodic Table are numbered from left to right as 1-18 (CRC Handbook of Chemistry and Physics, 81$^{st}$ Edition, 2000).

2. Chrysene Compound

An embodiment of the present disclosure is a composition of Formula

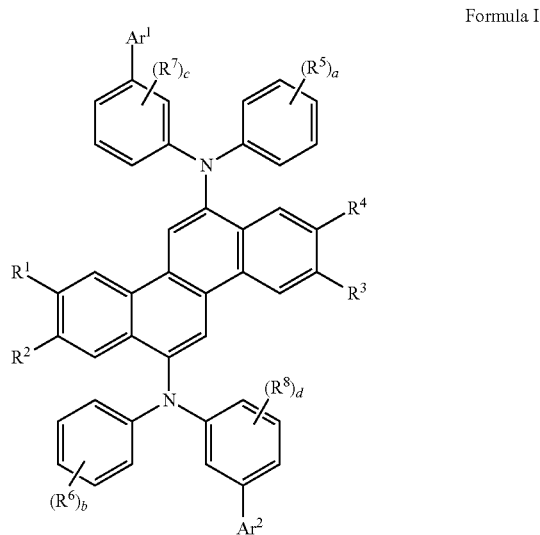

Formula I wherein:
R$^1$, R$^2$, R$^3$ and R$^4$ are the same or different and are selected from the group consisting of H, D, alkyl, and silyl, where R$^1$ and R$^2$ groups or R$^3$ and R$^4$ groups may be joined together to form a 5- or 6-membered aliphatic ring;

R$^5$ and R$^6$ are the same or different and are selected from the group consisting of D, alkyl, silyl, phenyl, naphthyl, carbazolyl, and fluorenyl;

R$^7$ and R$^8$ are the same or different at each occurrence and are selected from the group consisting of D, alkyl, alkoxy, silyl, siloxane, phenyl, biphenyl, and N-carbazolyl, or two adjacent R$^7$ groups or two adjacent R$^8$ groups can join together to form a naphthyl group;

Ar$^1$ and Ar$^2$ are the same or different and are aryl groups;

a and b are the same or different and are an integer from 1-5; and c and d are the same or different at each occurrence and are an integer from 0-4.

The compound is capable of blue emission.

The chrysene compounds described herein have a meta-substituted phenyl ring on the amino nitrogens, where the meta substituent is an aryl group. The compounds exhibit good lifetimes in electronic devices and emit blue light. The color is determined as the x- and y-coordinates according to the C.I.E. chromaticity scale (Commission Internationale de l'Eclairage, 1931). By "blue" it is meant that the color coordinates of electroluminescence have x≤0.145 and y≤0.14.

In some embodiments, R$^1$ through R$^4$ are hydrocarbon alkyl groups. In some embodiments R$^1$ is a branched hydrocarbon alkyl group and R$^2$ through R$^4$ are H. In some embodiments, the branched hydrocarbon alkyl group has from 3-8 carbon atoms. In some embodiments, the branched hydrocarbon alkyl group is a secondary alkyl selected from the group consisting of isopropyl and 2-butyl. In some embodiments, the branched hydrocarbon alkyl group is a tertiary alkyl selected from the group consisting of t-butyl and 2-(2-methyl)-butyl.

In some embodiments, $R^1$ and $R^2$ taken together and $R^3$ and $R^4$ taken together form a 5- or 6-membered aliphatic ring. In some embodiments, the aliphatic ring is selected from the group consisting of cyclohexyl and cyclopentyl. In some embodiments, the aliphatic ring has one or more alkyl substituents. In some embodiments, $R^1$ and $R^2$ taken together form a 5- or 6-membered aliphatic ring and $R^3$ and $R^4$ are H.

In some embodiments, each of $R^1$ through $R^4$ is H.

In some embodiments, $R^5$ and $R^6$ are straight chain or branched alkyl groups. In some embodiments, $R^5$ and $R^6$ are straight chain or branched hydrocarbon alkyl groups. In some embodiments, $R^5$ and $R^6$ are hydrocarbon alkyl groups having 1-6 carbon atoms. In some embodiments, c=d=1, and $R^5$ and $R^6$ are at the 4-position. The term "4-position" refers to the carbon which is pare to the nitrogen-bearing carbon. In some embodiments, c=d=2, and $R^5$ and $R^6$ are at the 2- and 4-positions. The term "2-position" refers to the carbon which is ortho to the nitrogen-bearing carbon.

In some embodiments, $R^5$ and $R^6$ are aromatic groups selected from the group consisting of o-phenyl, m-phenyl, p-phenyl, m-N-carbazolyl, p-N-carbazolyl, and 2-fluorenyl groups. By m-N-carbazolyl is meant the group

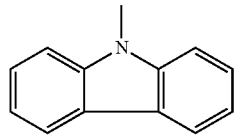

attached to the 3 position of the phenyl ring of the target molecule. By p-N-carbazolyl is meant the above group attached to the 4 position of the phenyl ring of the target molecule. By 2-fluorenyl is meant the group

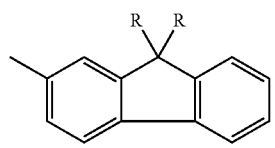

where R is H or alkyl. The 2-fluorenyl group can be meta or pare to the nitrogen-bearing carbon. The aromatic groups may further be substituted with D, alkyl, silyl, or phenyl groups.

In some embodiments, $R^7$ and $R^8$ are selected from hydrocarbon alkyl groups having 1-10 carbon atoms. In some embodiments, a and b are 1 and the $R^7$ and $R^8$ are pare to the nitrogen bearing carbon. In some embodiments, a and b are 2 and the two $R^7$ and $R^8$ groups are pare and ortho to the nitrogen bearing carbon.

In some embodiments, $Ar^1$ and $Ar^2$ are selected from the group consisting of phenyl, naphthyl, N-carbazolyl, N-carbazolylphenyl, and a group having Formula II:

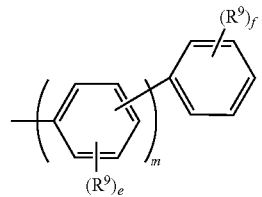

Formula II where:
$R^9$ is the same or different at each occurrence and is selected from the group consisting of D, alkyl, alkoxy, silyl, siloxane, and aryl;

e is the same or different at each occurrence and is an integer from 0-4;

f is the same or different at each occurrence and is an integer from 0-5; and m is the same or different at each occurrence and is an integer from 0 to 6.

By "N-carbazolylphenyl" is meant the group

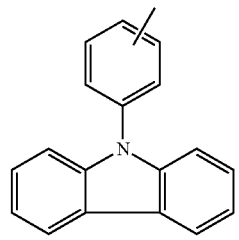

The carbazolylphenyl group can be meta or para to the nitrogen-bearing carbon. The group may further be substituted with D, alkyl, silyl, or phenyl groups.

In some embodiments. $Ar^1$ and $Ar^2$ have Formula IIa:

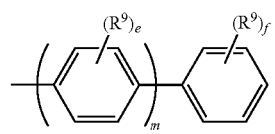

Formula IIa where $R^9$, e, f and m are as defined above.

In some embodiments of Formula I, $R^7$ and $R^8$ are selected from the group consisting of D, phenyl, biphenyl, and N-carbazolyl, or two adjacent $R^7$ groups or two adjacent $R^8$ groups can join together to form a naphthyl group. Surprisingly and unexpectedly, compounds having these $R^7$ and $R^8$ groups have been found to emit deep blue light. The color is determined as the x- and y-coordinates according to the C.I.E. chromaticity scale (Commission Internationale de l'Eclairage, 1931). By "deep blue" it is meant that the color coordinates of electroluminesence have x≤0.145 and y≤0.128. A deep blue emitter is needed in order to achieve the desired color gamut for many display applications.

In some embodiments, the chrysene compound is selected from compounds E1 through E7:
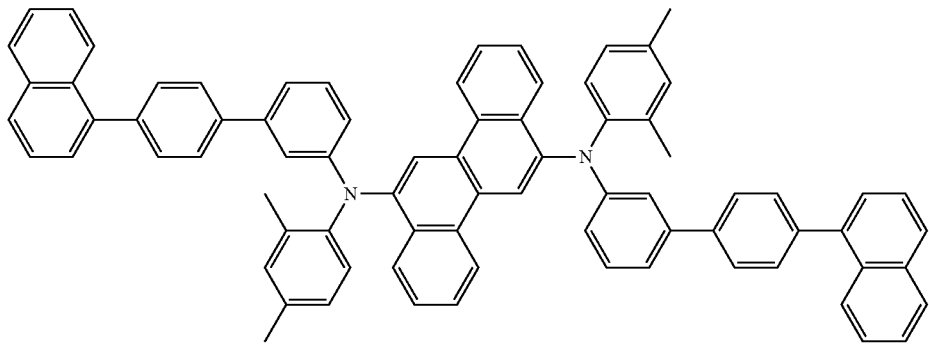
E1
$C_{78}H_{58}N_2$
Exact Mass: 1022.46
Mol. Wt.: 1023.31
C, 91.55; H, 5.71; N, 2.74
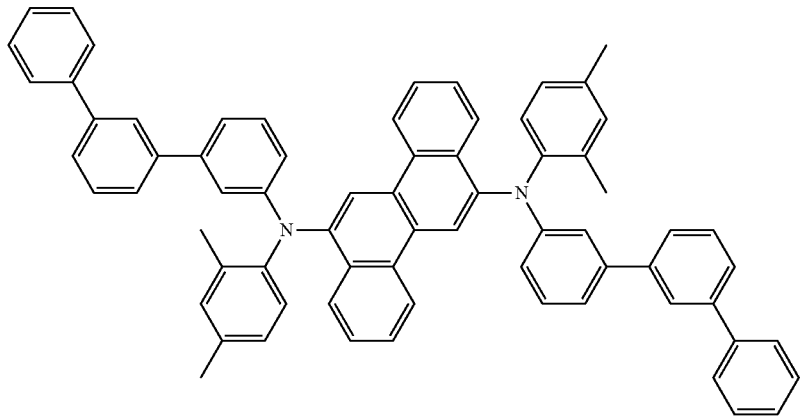
E2
$C_{70}H_{54}N_2$
Exact Mass: 922.43
Mol. Wt.: 923.19
C, 91.07; H, 5.90; N, 3.03
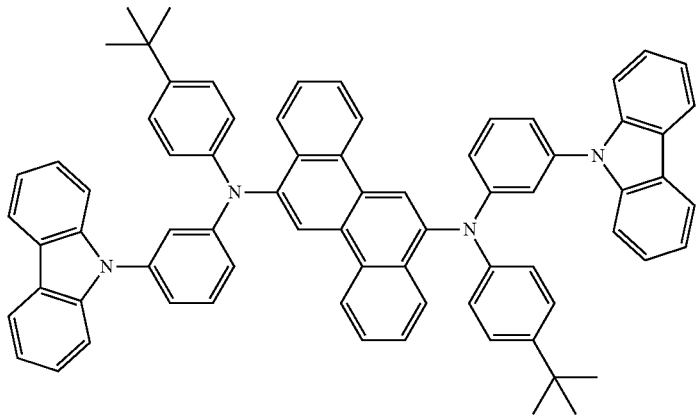
E3
$C_{74}H_{60}N_4$
Exact Mass: 1004.48
Mol. Wt.: 1005.30
C, 88.41; H, 6.02; N, 5.57

E4
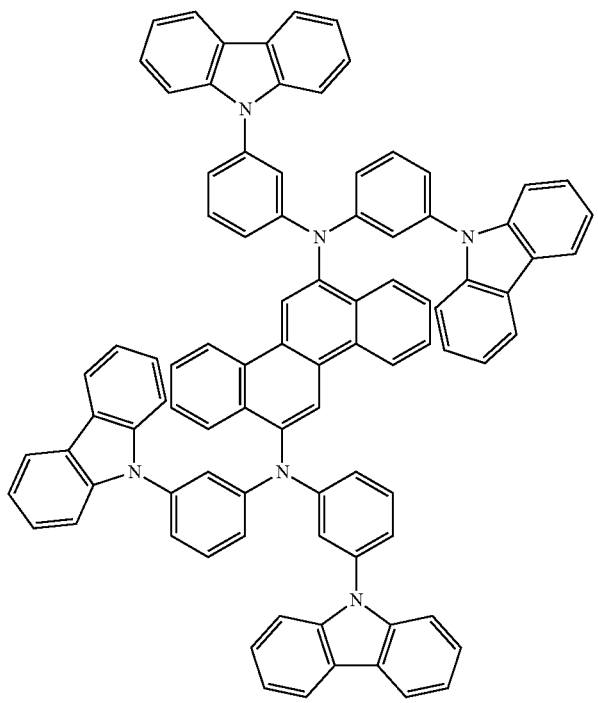
C₉₀H₅₈N₆
Exact Mass: 1222.47
Mol. Wt.: 1223.46
C, 88.35; H, 4.78; N, 6.87
E5
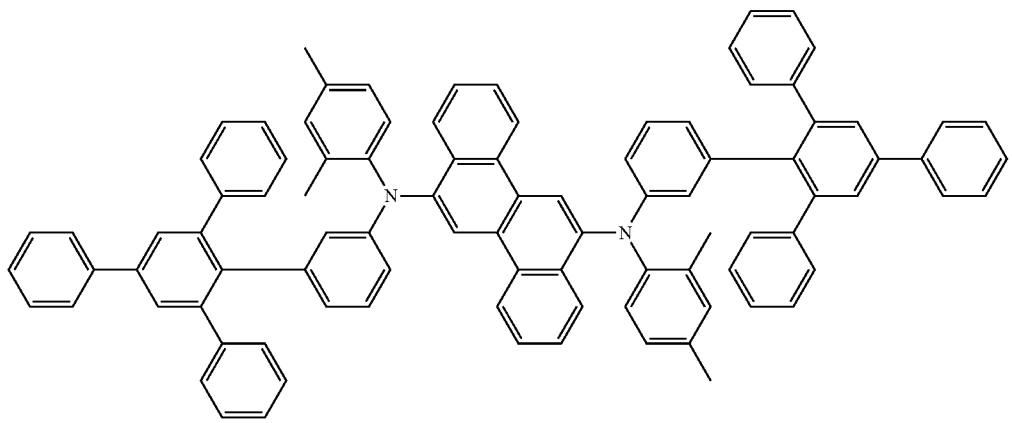
E6
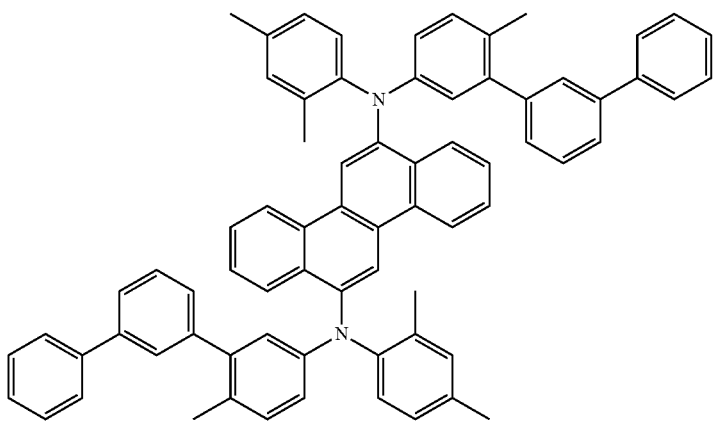

-continued

E7

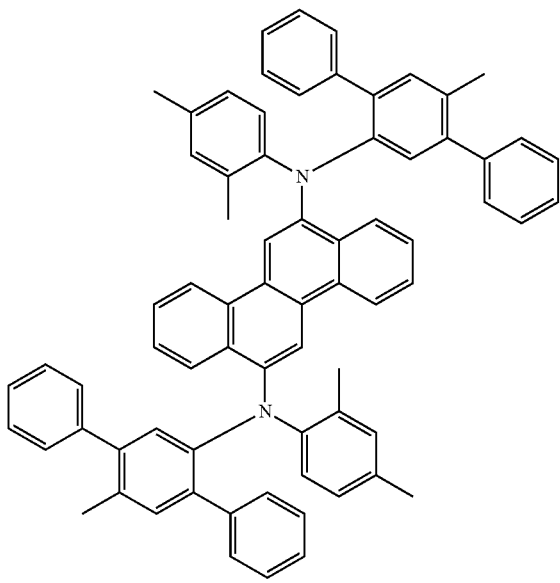

The new chrysenes can be prepared by known coupling and substitution reactions. Exemplary preparations are given in the Examples.

The chrysene compounds described herein can be formed into films using liquid deposition techniques. Thin films of these materials dispersed in a host matrix exhibit good to excellent photoluminescent properties and blue emission.

3. Electronic Device

Organic electronic devices that may benefit from having one or more layers comprising the blue luminescent materials described herein include, but are not limited to, (1) devices that convert electrical energy into radiation (e.g., a light-emitting diode, light emitting diode display, or diode laser), (2) devices that detect signals through electronics processes (e.g., photodetectors, photoconductive cells, photoresistors, photoswitches, phototransistors, phototubes, IR detectors), (3) devices that convert radiation into electrical energy, (e.g., a photovoltaic device or solar cell), and (4) devices that include one or more electronic components that include one or more organic semi-conductor layers (e.g., a transistor or diode).

One illustration of an organic electronic device structure is shown in FIG. 1. The device 100 has a first electrical contact layer, an anode layer 110 and a second electrical contact layer, a cathode layer 160, and a photoactive layer 140 between them. Adjacent to the anode is a buffer layer 120. Adjacent to the buffer layer is a hole transport layer 130, comprising hole transport material. Adjacent to the cathode may be an electron transport layer 150, comprising an electron transport material. As an option, devices may use one or more additional hole injection or hole transport layers (not shown) next to the anode 110 and/or one or more additional electron injection or electron transport layers (not shown) next to the cathode 160.

Layers 120 through 150 are individually and collectively referred to as the active layers.

In one embodiment, the different layers have the following range of thicknesses: anode 110, 500-5000 Å, in one embodiment 1000-2000 Å; buffer layer 120, 50-2000 Å, in one embodiment 200-1000 Å; hole transport layer 130, 50-2000 Å, in one embodiment 200-1000 Å; photoactive layer 140, 10-2000 Å, in one embodiment 100-1000 Å; layer 150, 50-2000 Å, in one embodiment 100-1000 Å; cathode 160, 200-10000 Å, in one embodiment 300-5000 Å. The location of the electron-hole recombination zone in the device, and thus the emission spectrum of the device, can be affected by the relative thickness of each layer. The desired ratio of layer thicknesses will depend on the exact nature of the materials used.

Depending upon the application of the device 100, the photoactive layer 140 can be a light-emitting layer that is activated by an applied voltage (such as in a light-emitting diode or light-emitting electrochemical cell), or a layer of material that responds to radiant energy and generates a signal with or without an applied bias voltage (such as in a photodetector). Examples of photodetectors include photoconductive cells, photoresistors, photoswitches, phototransistors, and phototubes, and photovoltaic cells, as these terms are described in Markus, John, *Electronics and Nucleonics Dictionary*, 470 and 476 (McGraw-Hill, Inc. 1966).

a. Photoactive Layer

The chrysene compounds of Formula I are useful as photoactive materials in layer 140. The compounds can be used alone, or in combination with a host material.

In some embodiments, the host is a bis-condensed cyclic aromatic compound.

In some embodiments, the host is an anthracene derivative compound. In some embodiments the compound has the formula:

An-L-An where:
An is an anthracene moiety;
L is a divalent connecting group.

In some embodiments of this formula, L is a single bond, —O—, —S—, N(R)—, or an aromatic group. In some embodiments, An is a mono- or diphenylanthryl moiety.

In some embodiments, the host has the formula:

A-An-A where:
An is an anthracene or deuterated anthracene moiety;
A is the same or different at each occurrence and is an aromatic group.

In some embodiments, the A groups are attached at the 9- and 10-positions of the anthracene moiety. In some embodiments, A is selected from the group consisting naphthyl, naphthylphenylene, naphthyinaphthylene, and deuterated derivatives thereof. In some embodiments the compound is symmetrical and in some embodiments the compound is non-symrnetrical.

In some embodiments, the host has the formula:

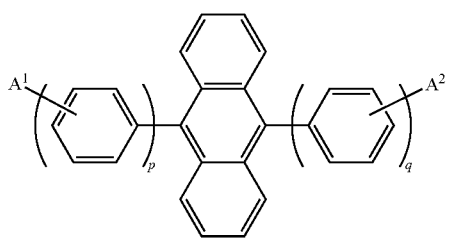

where:

$A^1$ and $A^2$ are the same or different at each occurrence and are selected from the group consisting of H, D, an aromatic group, and an alkenyl group, or A may represent one or more fused aromatic rings;

p and q are the same or different and are an integer from 1-3.

In some embodiments, the anthracene derivative is non-symmetrical. In some embodiments, p=2 and q=1. In some embodiments, at least one of $A^1$ and $A^2$ is a naphthyl group or deuterated naphthyl group.

In some embodiments, the host is selected from the group consisting of

H1

H2

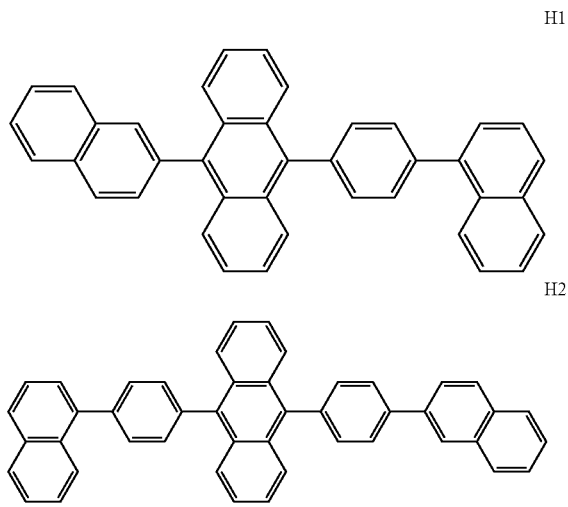

and combinations thereof.

The chrysene compounds of Formula I, in addition to being useful as emissive dopants in the photoactive layer, can also act as charge carrying hosts for other emissive dopants in the photoactive layer 140. The chrysene compounds can be used as the sole host material or in combination with one or more additional host materials.

b. Other Device Layers

The other layers in the device can be made of any materials that are known to be useful in such layers.

The anode 110, is an electrode that is particularly efficient for injecting positive charge carriers. It can be made of, for example, materials containing a metal, mixed metal, alloy, metal oxide or mixed-metal oxide, or it can be a conducting polymer, or mixtures thereof. Suitable metals include the Group 11 metals, the metals in Groups 4-6, and the Group 8-10 transition metals. If the anode is to be light-transmitting, mixed-metal oxides of Groups 12, 13 and 14 metals, such as indium-tin-oxide, are generally used. The anode 110 can also comprise an organic material such as polyaniline as described in "Flexible light-emitting diodes made from soluble conducting polymer," Nature vol. 357, pp 477-479 (11 Jun. 1992). At least one of the anode and cathode is desirably at least partially transparent to allow the generated light to be observed.

The buffer layer 120 comprises buffer material and may have one or more functions in an organic electronic device, including but not limited to, planarization of the underlying layer, charge transport and/or charge injection properties, scavenging of impurities such as oxygen or metal ions, and other aspects to facilitate or to improve the performance of the organic electronic device. Buffer materials may be polymers, oligomers, or small molecules. They may be vapour deposited or deposited from liquids which may be in the form of solutions, dispersions, suspensions, emulsions, colloidal mixtures, or other compositions.

The buffer layer can be formed with polymeric materials, such as polyaniline (PAM) or polyethylenedioxythiophene (PEDOT), which are often doped with protonic acids. The protonic acids can be, for example, poly(styrenesulfonic acid), poly(2-acrylamido-2-methyl-1-propanesulfonic acid), and the like.

The buffer layer can comprise charge transfer compounds, and the like, such as copper phthalocyanine and the tetrathiafulvalene-tetracyanoquinodimethane system (TTF-TCNQ).

In some embodiments, the buffer layer comprises at least one electrically conductive polymer and at least one fluorinated acid polymer. Such materials have been described in, for example, published U.S. patent applications 2004-0102577, 2004-0127637, and 2005/205860

Examples of hole transport materials for layer 130 have been summarized for example, in Kirk-Othmer Encyclopedia of Chemical Technology, Fourth Edition, Vol. 18, p. 837-860, 1996, by Y. Wang. Both hole transporting molecules and polymers can be used. Commonly used hole transporting molecules are: N,N-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis-(3-methylphenyl)-N,N,N',N'-2,5-phenylenediamine (PDA), a-phenyl-4-N,N-diphenylaminostyrene (TPS), p-(diethylamino)benzaldehyde diphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl]pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), N,N'-bis(naphthalen-1-yl)-N,N'-bis-(phenyl)benzidine (α-NPB), and porphyrinic compounds, such as copper phthalocyanine. Commonly used hole transporting polymers are polyvinylcarbazole, (phenylmethyl)polysilane, and polyaniline. It is also possible to obtain hole transporting polymers by doping hole transporting molecules such as those mentioned above into polymers such as polystyrene and polycarbonate. In some cases, triarylamine polymers are used, especially triarylamine-fluorene copolymers. In some cases, the polymers and copolymers are crosslinkable.

Examples of additional electron transport materials which can be used in layer 150 include metal chelated oxinoid compounds, such as tris(8-hydroxyquinolato)aluminum (Alq$_3$); bis(2-methyl-8-quinolinolato)(para-phenyl-phenolato)aluminum(III) (BAlQ)); and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ), and 1,3,5-tri(phenyl-2-benzimidazole)benzene (TPBI); quinoxaline derivatives such as 2,3-bis(4-fluorophenyl)quinoxaline; phenanthroline derivatives such as 9,10-diphenylphenanthroline (DPA) and 2,9-dimethyl-4,7-diphenyl-1,10-phenanthroline (DDPA); and mixtures thereof. Layer 150 can function both to facilitate electron transport, and also serve as a buffer layer or confinement layer to prevent quenching of the exciton at layer interfaces. Preferably, this layer promotes electron mobility and reduces exciton quenching.

The cathode 160, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used. Li-containing organometallic compounds, LiF, and Li$_2$O can also be deposited between the organic layer and the cathode layer to lower the operating voltage.

It is known to have other layers in organic electronic devices. For example, there can be a layer (not shown) between the anode 110 and buffer layer 120 to control the amount of positive charge injected and/or to provide bandgap matching of the layers, or to function as a protective layer. Layers that are known in the art can be used, such as copper phthalocyanine, silicon oxy-nitride, fluorocarbons, silanes, or an ultra-thin layer of a metal, such as Pt. Alternatively, some or all of anode layer 110, active layers 120, 130, 140, and 150, or cathode layer 160, can be surface-treated to increase charge carrier transport efficiency. The choice of materials for each of the component layers is preferably determined by balancing the positive and negative charges in the emitter layer to provide a device with high electroluminescence efficiency.

It is understood that each functional layer can be made up of more than one layer.

The device can be prepared by a variety of techniques, including sequential vapor deposition of the individual layers on a suitable substrate. Substrates such as glass, plastics, and metals can be used. Conventional vapor deposition techniques can be used, such as thermal evaporation, chemical vapor deposition, and the like. Alternatively, the organic layers can be applied from solutions or dispersions in suitable solvents, using conventional coating or printing techniques, including but not limited to spin-coating, dip-coating, roll-to-roll techniques, ink-jet printing, screen-printing, gravure printing and the like.

The present invention also relates to an electronic device comprising at least one active layer positioned between two electrical contact layers, wherein the at least one active layer of the device includes the chrysene compound of Formula 1. Devices frequently have additional hole transport and electron transport layers.

To achieve a high efficiency LED, the HOMO (highest occupied molecular orbital) of the hole transport material desirably aligns with the work function of the anode, and the LUMO (lowest un-occupied molecular orbital) of the electron transport material desirably aligns with the work function of the cathode. Chemical compatibility and sublimation temperature of the materials are also important considerations in selecting the electron and hole transport materials.

It is understood that the efficiency of devices made with the chrysene compounds described herein, can be further improved by optimizing the other layers in the device. For example, more efficient cathodes such as Ca, Ba or LiF can be used. Shaped substrates and novel hole transport materials that result in a reduction in operating voltage or increase quantum efficiency are also applicable. Additional layers can also be added to tailor the energy levels of the various layers and facilitate electroluminescence.

The chrysene compounds of the invention often are fluorescent and photoluminescent and can be useful in applications other than OLEDs, such as oxygen sensitive indicators and as fluorescent indicators in bioassays.

EXAMPLES

The following examples illustrate certain features and advantages of the present invention. They are intended to be illustrative of the invention, but not limiting. All percentages are by weight, unless otherwise indicated.

Example 1

This example illustrates the preparation of Compound E1, N6,N12-bis(2,4-dimethylphenyl)-N6,N12-bis(4'-(naphthalen-1yl)biphenyl-4-yl) chrysene-6,12-diamine.

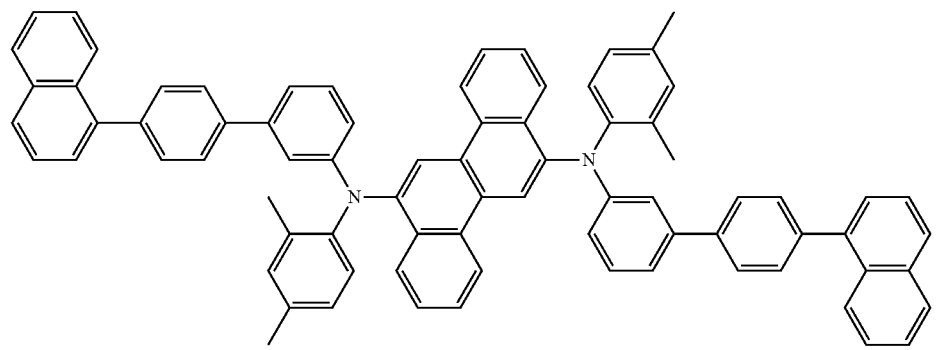

$C_{78}H_{58}N_2$
Exact Mass: 1022.46
Mol. Wt.: 1023.31
C, 91.55; H, 5.71; N, 2.74

In a drybox, 6,12-dibromochrysene (0.27 g, 0.69 mmol), N-(2,4-dimethylphenyl)-N-(4'-(naphthalen-1-yl)biphenyl-4-yl)amine (0.60 g, 1.41 mmol), tris(tert-butyl)phosphine (0.042 g, 0.21 mmol) and tris(dibenzylideneacetone)dipalladium(0) (0.094 g, 0.103 mmol) were combined in round bottom flask and dissolved in 20 ml of dry toluene. The solution was stirred for a minute and followed by sodium tert-butoxide (0.145 g, 1.51 mmol) and 10 ml of dry toluene. A heating mantle was added and the reaction heated to 60 C for 18 hours. The reaction mixture was then cooled to room temperature and filtered through a 1 inch plug of silica gel and one inch of celite, washing with toluene (500 mL). Removal of volatiles under reduced pressure gave a yellow solid. The crude product was purified further by silica gel column chromatography using a gradient of chloroform in hexanes (0% to 20%). Recrystallization from DCM and acetonitrile yielded 0.400 g (60%) of product as a yellow solid. $^1$H NMR (CDCl$_3$) is consistent with structure.

Example 2

This example illustrates the preparation of Compound E2, N6,N12-bis(4-(biphenyl-3-yl)phenyl-2-yl)-N6,N12-bis(2,4-dimethylphenyl)chrysene-6,12-diamine.

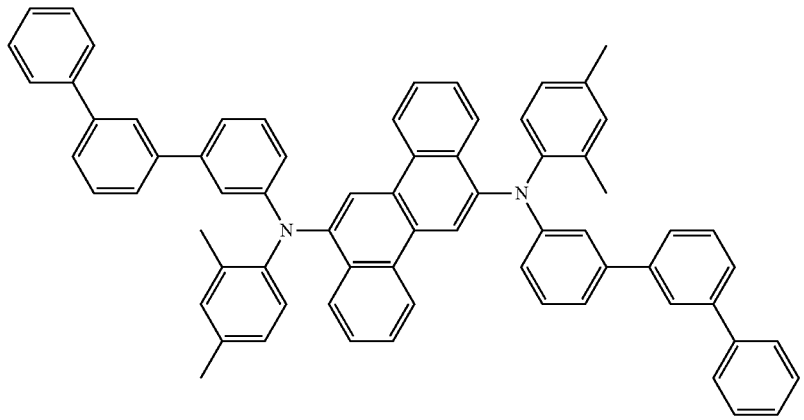

$C_{70}H_{54}N_2$
Exact Mass: 922.43
Mol. Wt.: 923.19
C, 91.07; H, 5.90; N, 3.03

In a drybox, 6,12-dibromochrysene (0.68 g, 1.75 mmol), N-(2,4-dimethylphenyl)-N-(4-(biphenyl-3-yl)phenyl-2-yl)amine (1.35 g, 3.67 mmol), tris(tert-butyl)phosphine (0.035 g, 0.175 mmol) and tris(dibenzylideneacetone)dipalladium(0) (0.080 g, 0.087 mmol) were combined in round bottom flask and dissolved in 15 ml of dry toluene. The solution was stirred for a minute and followed by sodium tert-butoxide (0.37 g, 3.84 mmol) and 5 ml of dry toluene. A heating mantle was added and the reaction heated to 60 C for 3 days. The reaction mixture was then cooled to room temperature and filtered through a 1 inch plug of silica gel and one inch of celite, washing with toluene (500 mL). Removal of volatiles under reduced pressure gave a yellow solid. The crude product was purified further by silica gel column chromatography using a gradient of chloroform in hexanes (0% to 40%). Recrystallization from DCM and acetonitrile yielded 0.900 g (59%) of product as a yellow solid. $^1$H NMR (CDCl$_3$) is consistent with structure.

Example 3

This example illustrates the preparation of Compound E3, N6,N12-bis(3-(9-carbazolyl)phenyl)-N6,N12-bis(4-t-butylphenyl)chrysene-6,12-diamine.

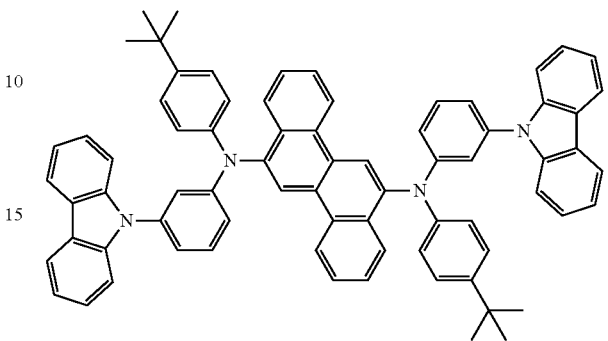

Take 0.39 g of dibromochrysene (1 mM) in a nitrogen filled glove box and add 0.80 g (2.1 mM) of the appropriate secondary amine (prepared as described above from 9-(3-Bromophenyl)-carbazole and 4-t-butylaniline) and 0.22 g t-BuONa (2.2 mM) with 10 mL xylenes. Add 0.15 g Pd$_2$DBA$_3$ (0.15 mM), 0.06 g P(t-Bu)$_3$ (0.30 mM) dissolved in 2 mL xylenes. Mix and heat in the glove box in a mantle at 110° C. under nitrogen for 1 hr. The solution immediately is dark purple but on reaching ~80° C. it is dark yellow brown with a noticeable blue luminescence. Cool to ~80 C and continue stirring overnight. Cool and work up by removing from the glove box and filtering through a basic-alumina/silica/florisil plug eluting with DCM/toluene 1/1. The blue luminescent material elutes from the column as a pale yellow solution. Evaporate to low volume and add diethylether to ppt a pale yellow solid with blue PL in ~1.0 g yield. TLC on silica gel shows single blue spot in toluene/hexanes. Material is modestly soluble in toluene and the structure is confirmed by 1-H nmr spectroscopy.

Example 4

This example illustrates the preparation of Compound E4, N6,N12-tetra(3-(9-carbazolyl)phenyl) chrysene-6,12-diamine.

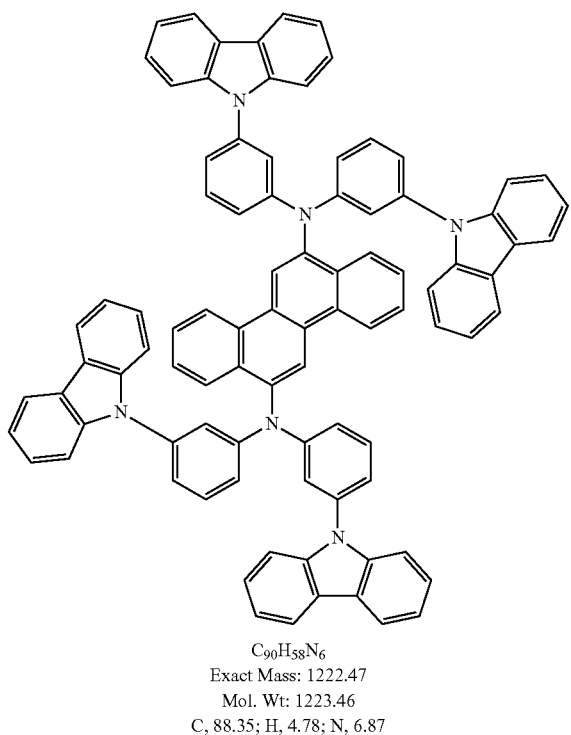 [SMILES: c1cc(N(c2cccc(-n3c4ccccc4c4ccccc43)c2)c2cc3c4ccccc4c(N(c4cccc(-n5c6ccccc6c6ccccc65)c4)c4cccc(-n5c6ccccc6c6ccccc65)c4)cc3c3ccccc23)cc(-n2c3ccccc3c3ccccc32)c1]

C<sub>90</sub>H<sub>58</sub>N<sub>6</sub>
Exact Mass: 1222.47
Mol. Wt: 1223.46
C, 88.35; H, 4.78; N, 6.87

Take 0.39 g of dibromochrysene (1 mM) in a nitrogen filled glove box and add 1.0 g (2.1 mM) of the appropriate secondary amine (made as described above from 9-(3-aminophenyl)carbazole and 9-(3-bromophenyl)carbazole) and 0.22 g t-BuONa (2.2 mM) with 10 mL xylenes. Add 0.15 g Pd$_2$DBA$_3$ (0.15 mM), 0.06 g P(t-Bu)$_3$ (0.30 mM) dissolved in 2 mL xylenes. Mix and heat in the glove box in a mantle at 110° C. under nitrogen for 1 hr. The solution immediately is dark purple but on reaching ~80° C. it is dark yellow brown with a noticeable blue luminescence. Cool to ~80° C. and continue stirring overnight. Cool to room temperature and work up by removing from glove box and filtering through a basic-alumina/silica/florisil plug eluting with DCM/toluene 1/1. The blue luminescent material elutes from the column as a pale yellow solution. Evaporate to low volume and add diethylether to ppt a pale yellow solid with blue PL in ~1.0 g yield. TLC on silica gel shows a single blue spot in toluene/hexanes. Material is quite soluble in toluene and the structure is confirmed by 1-H nmr spectroscopy.

Compounds E5-E7 and comparative Compound A, below, were made using synthetic techniques analogous to those described above.

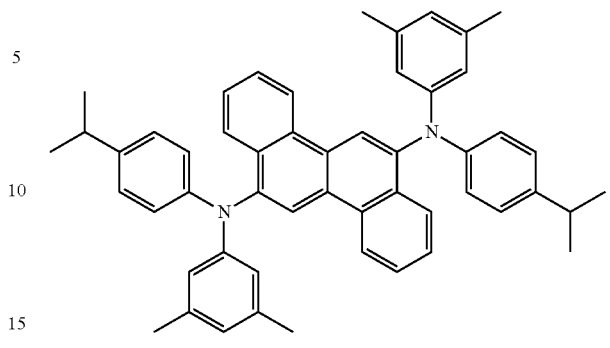

Compound A

Example 5

This example demonstrates the fabrication and performance of a device having deep blue emission. The following materials were used:

anode=Indium Tin Oxide (50 nm)
buffer layer=Buffer 1 (50 nm), which is an aqueous dispersion of an electrically conductive polymer and a polymeric fluorinated sulfonic acid. Such materials have been described in, for example, published U.S. patent applications US 2004/0102577, US 2004/0127637, and US 2005/0205860.
hole transport layer=HT-1, a bi-naphthalene polymer (20 nm)
photoactive layer=13:1 weight ratio of host H1:dopant (60 nm). The dopants are given in the table.
electron transport layer=a metal quinolate derivative (10 nm)
cathode=CsF/Al (0.7/100 nm)

OLED devices were fabricated by a combination of solution processing and thermal evaporation techniques. Patterned indium tin oxide (ITO) coated glass substrates from Thin Film Devices, Inc were used. These ITO substrates are based on Corning 1737 glass coated with ITO having a sheet resistance of 30 ohms/square and 80% light transmission. The patterned ITO substrates were cleaned ultrasonically in aqueous detergent solution and rinsed with distilled water. The patterned ITO was subsequently cleaned ultrasonically in acetone, rinsed with isopropanol, and dried in a stream of nitrogen.

Immediately before device fabrication the cleaned, patterned ITO substrates were treated with UV ozone for 10 minutes. Immediately after cooling, an aqueous dispersion of Buffer 1 was spin-coated over the ITO surface and heated to remove solvent. After cooling, the substrates were then spin-coated with a solution of a hole transport material, and then heated to remove solvent. After cooling the substrates were spin-coated with the emissive layer solution, and heated to remove solvent. The substrates were masked and placed in a vacuum chamber. An electron transport layer was deposited by thermal evaporation, followed by a layer of CsF. Masks were then changed in vacuo and a layer of Al was deposited by thermal evaporation. The chamber was vented, and the devices were encapsulated using a glass lid, dessicant, and UV curable epoxy.

The emission color coordinates were determined with a spectroradiometer. The results are given in Table 1.

TABLE 1

Device summary

| Example | Dopant | Color x-coordinate | y-coordinate |
|---|---|---|---|
| Comparative A | Compound A | 0.135 | 0.132 |
| Example 5 | E3 | 0.143 | 0.109 |

The x and y color coordinates are according to the C.I.E. chromaticity scale (Commission Internationale de l'Eclairage, 1931).

Example 6

This example demonstrates the fabrication and performance of a device having deep blue emission.

The devices were made as described in Example 5, except that the anode had a thickness of 180 nm. The results are given in Table 2.

TABLE 2

Device summary

| Example | Dopant | Color x-coordinate | y-coordinate |
|---|---|---|---|
| Comparative B | Compound A | 0.133 | 0.131 |
| Example 6 | E4 | 0.143 | 0.119 |

The x and y color coordinates are according to the C.I.E. chromaticity scale (Commission Internationale de L'Eclairage, 1931).

Examples 7-9

These examples demonstrate the fabrication and performance of devices having deep blue emission.

The devices were made as described in Example 5, except that the buffer layer had a thickness of 25 nm and the photoactive layer had a thickness of 48 nm. The results are given in Table 3.

TABLE 3

Device summary

| Example | Dopant | Color x-coordinate | y-coordinate |
|---|---|---|---|
| Comparative C | Compound A | 0.138 | 0.135 |
| Example 7 | E1 | 0.142 | 0.119 |
| Example 8 | E2 | 0.143 | 0.110 |
| Example 9 | E5 | 0.142 | 0.122 |

The x and y color coordinates are according to the C.I.E. chromaticity scale (Commission Internationale de l'Eclairage, 1931).

Examples 10-13

These examples demonstrate the fabrication and performance of devices having blue or deep blue emission.

The devices were made as described in Example 5, except that HT-2 was used for the hole transport layer and the photoactive layer had a thickness of 40 nm. HT-2 is a different bi-naphthalene polymer. The results are given in Table 4.

TABLE 4

Device summary

| Example | Dopant | Color x-coordinate | y-coordinate |
|---|---|---|---|
| Comparative D | Compound A | 0.136 | 0.113 |
| Example 10 | E2 | 0.139 | 0.097 |
| Example 11 | E6 | 0.134 | 0.131 |
| Example 12 | E7 | 0.138 | 0.118 |

The x and y color coordinates are according to the C.I.E. chromaticity scale (Commission Internationale de l'Eclairage, 1931).

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment Conversely, various features that are, for brevity, described in the context of a single embodiment, may also be provided separately or in any subcombination. Further, reference to values stated in ranges include each and every value within that range.

What is claimed is:

1. A compound selected from E1 through E7.
2. An organic electronic device comprising a first electrical contact layer, a second electrical contact layer, and at least one active layer therebetween, wherein the active layer comprises a compound selected from E1 through E7.
3. The device of claim 2, wherein the active layer is a photoactive layer and further comprises a host material.
4. The device of claim 2, further comprising a buffer layer between the first electrical contact layer and the active layer.
5. The device of claim 4, wherein the buffer layer comprises at least one electrically conductive polymer and at least one fluorinated acid polymer.

* * * * *